US007427683B2

(12) United States Patent
Player et al.

(10) Patent No.: US 7,427,683 B2
(45) Date of Patent: Sep. 23, 2008

(54) C-FMS KINASE INHIBITORS

(75) Inventors: Mark R. Player, Phoenixville, PA (US); Nand Baindur, Kendall Park, NJ (US); Benjamin Brandt, Philadelphia, PA (US); Naresh Chadha, Montville, NJ (US); Raymond J. Patch, Yardley, PA (US); Davoud Asgari, Plainsboro, NJ (US); Taxiarchis Georgiadis, Carmel, IN (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 307 days.

(21) Appl. No.: 10/970,865

(22) Filed: Oct. 22, 2004

(65) Prior Publication Data
US 2005/0131022 A1 Jun. 16, 2005

Related U.S. Application Data

(63) Continuation-in-part of application No. 10/831,216, filed on Apr. 26, 2004.

(60) Provisional application No. 60/465,204, filed on Apr. 25, 2003.

(51) Int. Cl.
A61K 31/454 (2006.01)
C07D 401/12 (2006.01)
(52) U.S. Cl. .................... 546/208; 514/326
(58) Field of Classification Search ............. 546/208; 514/326
See application file for complete search history.

(56) References Cited
U.S. PATENT DOCUMENTS

| | | | |
|---|---|---|---|
| 3,717,579 A * | 2/1973 | Hofmann et al. ............ 514/352 |
| 3,862,152 A | 1/1975 | Kuwada et al. |
| 4,172,947 A | 10/1979 | Warner, Jr. et al. |
| 4,186,199 A | 1/1980 | Glamkowski et al. |
| 5,258,357 A | 11/1993 | Muenster et al. |
| 5,854,285 A * | 12/1998 | Sriram et al. ............... 514/514 |
| 6,380,247 B2 | 4/2002 | Konishi et al. |
| 6,420,567 B1 | 7/2002 | Wu et al. |
| 6,545,161 B2 * | 4/2003 | Gupta et al. ............ 548/263.2 |
| 6,936,736 B2 | 8/2005 | Ikeda et al. |
| 7,012,094 B1 | 3/2006 | Bertenshaw et al. |
| 7,019,024 B2 | 3/2006 | Ognyanov et al. |
| 7,037,937 B2 | 5/2006 | Uckun et al. |
| 7,041,702 B1 | 5/2006 | Durant et al. |
| 7,045,551 B2 | 5/2006 | Wu et al. |
| 7,087,604 B2 | 8/2006 | Cherney |
| 7,098,240 B2 | 8/2006 | Griffiths et al. |
| 7,105,564 B1 | 9/2006 | Honma et al. |
| 7,109,243 B2 | 9/2006 | Liu et al. |
| 7,115,660 B2 | 10/2006 | Boger et al. |
| 7,179,840 B2 | 2/2007 | Rieck et al. |
| 2005/0004112 A1 | 1/2005 | Player et al. |
| 2005/0113566 A1 | 5/2005 | Player et al. |
| 2005/0131022 A1 | 6/2005 | Player et al. |

FOREIGN PATENT DOCUMENTS

| | | |
|---|---|---|
| DE | 26 35 818 A1 | 11/1977 |
| EP | 1 193 246 A1 | 4/2002 |
| GB | 1 508 947 | 4/1978 |
| WO | WO 95/19169 A2 | 7/1995 |
| WO | WO 00/27820 A | 5/2000 |
| WO | WO 00/62778 A1 | 10/2000 |
| WO | WO 02/28825 A | 4/2002 |
| WO | WO 02/068406 A | 9/2002 |
| WO | WO 03/103648 A1 | 12/2003 |
| WO | WO 03/103658 A1 | 12/2003 |
| WO | WO 2004/018461 A | 3/2004 |
| WO | WO 2004/022525 A | 3/2004 |
| WO | WO 2004/096795 A | 11/2004 |
| WO | WO 2006/047277 A2 | 5/2006 |
| WO | WO 2006/047504 A1 | 5/2006 |

OTHER PUBLICATIONS

CAS accerssion No. 1973:132353, Registry No. 41235-81-8 (attached hereto).*
Nilsson et al, J. Comb. Chem. vol. 3, p. 546-553 (2001).*
Database Chemcats, Chemical Abstracts Service, Columbus, Ohio, US; XP002307086, Order Nos. t0370-0639, t0369-0732, & "Ambinter Stock Screening Collection", Jan. 1, 2004, Ambinter, 46 Quai Loius Bleriot, F-75016 Paris, France.
WO 03/103648A (Muto et al; Inst of Medicinal Molecular) Dec. 18, 2003, Abstract; & Database Chemabs 'Online! Chemical Abstracts Service, Columbus, Ohio, US; XP002307087, retrieved from STN Database accession No. 140:27850 Abstract; and RN's 439144-91-9, 634185-05-0, 634185-10-7, 634185-14-1.
WO 03/103658A (Muto et al; Inst of Medicinal Molecular) Dec. 18, 2003, Abstract; & Database Chemabs 'Online! Chemical Abstracts Service, Columbus, Ohio, US; XP002307891, retrieved from STN Database accession No. 140:42204 Abstract; and RN's 439144-91-9, 634185-05-0, 634185-10-7, 634185-14-1.

(Continued)

Primary Examiner—Bernard Dentz

(57) ABSTRACT

The invention is directed to compounds of Formulae I:

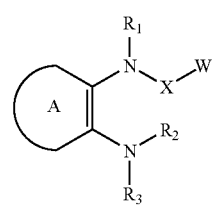

wherein A, $R_1$, $R_2$, $R_3$, $R_4$, X, and W are set forth in the specification, as well as solvates, hydrates, tautomers or pharmaceutically acceptable salts thereof, that inhibit protein tyrosine kinases, especially c-fms kinase.

4 Claims, No Drawings

OTHER PUBLICATIONS

Database Chemcats, Chemical Abstracts Service, Columbus, Ohio, US; XP002307088, Order No. CHS2296111. & "ChemStar Product List" Apr. 24, 2003, Chemstar Ltd, Leningradskii Prospekt 47, Office 465, Moskow, 125167, Russia.

Database Beilstein, Beilstein Institute for Organic Chemistry, Frankfurt-Main, DE; XP002307089, Database Accession No. 290139 (BRN). & Chem. Ber., vol. 24, 1891, p. 2101.

Database Beilstein, Beilstein Institute for Organic Chemistry, Frankfurt-Main, DE; XP002307090, Database Accession Nos. 1012247, 1257241, 1319746, 1322924 (BRN's). & J. Chem. Soc., 1963, pp. 4666-4669.

Database Beilstein, Beilstein Institute for Organic Chemistry, Frankfurt-Main, DE; XP002307091, Database Accession Nos. 551856, 578613, 1257241, 1322924, 1324197 (BRN's). & J. Chem. Soc., 1964, p. 2609.

Database Beilstein, Beilstein Institute for Organic Chemistry, Frankfurt-Main, DE; XP002307092, Database Accession Nos. 1601543, 2983204, 2982987 (BRN's). & J. Chem. Soc. C, 1969, pp. 1444-1448.

Database Beilstein, Beilstein Institute for Organic Chemistry, Frankfurt-Main, DE; XP002307093, Database Accession Nos. 702242, 705174, 715898 (BRN's). & Justus Liebigs Ann. Chem., vol. 699, 1966, p. 88.

Database Beilstein, Beilstein Institute for Organic Chemistry, Frankfurt-Main, DE; XP002307094, Database Accession Nos. 126414, 1662045 (BRN's). & J. Chem. Soc. B, 1971, p. 696.

Database Beilstein, Beilstein Institute for Organic Chemistry, Frankfurt-Main, DE; XP002307095, Database Accession Nos. 5608933, 5609095 (BRN's). & Chem. Pharm. Bull., vol. 31, No. 9, 1983, pp. 3160-3167.

Database Beilstein, Beilstein Institute for Organic Chemistry, Frankfurt-Main, DE; XP002307096, Database Accession No. 5966001 (BRN). & Chem. Pharm. Bull., vol. 36, No. 9, 1988, pp. 3248-3252.

Melik-Organdzhanyan et al.: "New Method for the Synthesis of Polyfunctional 5-Aminopyrimidines", Chem. Heterocycl. Compd. Engl. Transl., 1983, pp. 100-102, XP009040286.

Yoshino et al: "Novel Sulfonamides as Potential, Systematically Active Antitumor Agents", J. Med. Chem., vol. 35, 1992, pp. 2496-2497, XP002307083.

Hodson et al.: "Alpha1-Adrenoceptor Activation: A Comparison of 4-(Anilinomethyl)imidazoles and 4-(Phenoxymethyl)imidazoles to Related 2-imidazolines", Bioorg. Med. Chem. Lett., vol. 12, 2002, pp. 3449-3452, XP002307084.

Database Beilstein, Beilstein Institute for Organic Chemistry, Frankfurt-Main, DE; XP002307097, Database Accession Nos. 282633, 402265, 403511 (BRN's). & Helv. Chim. Acta, vol. 61, 1978, p. 2887.

Database Beilstein, Beilstein Institute for Organic Chemistry, Frankfurt-Main, DE; XP002307098, Database Accession Nos. 6972518, 6973696, 6974212, 6975313, 6975875 (BRN's). & Farmaco Ed. Sci., vol. 42, No. 3, 1987, pp. 231-236.

Database Beilstein, Beilstein Institute for Organic Chemistry, Frankfurt-Main, DE; XP002307099, Database Accession Nos. 1112966, 1378557, 1384830, 2732875, 2743259, 2743836, 2746021, 2752729, 2755871, 2774906 (BRN's). & Bull. Soc. Chim. Fr., 1973, pp. 3017-2018.

Database Beilstein, Beilstein Institute for Organic Chemistry, Frankfurt-Main, DE; XP002307100, Database Accession Nos. 4875002, 4878430, 4878634, 4880771, 4881664, 4884524 (BRN's). & J. Med. Chem., vol. 35, no. 5, 1992, pp. 804-807.

Database Beilstein, Beilstein Institute for Organic Chemistry, Frankfurt-Main, DE; XP002307101, Database Accession No. 177103 (BRN). & Arh. Chem., vol. 27, 1955, p. 33.

Database Beilstein, Beilstein Institute for Organic Chemistry, Frankfurt-Main, DE; XP002307102, Database Accession Nos. 28308, 252444 (BRN's). & Proc.-Indian Acad. Sci. Sect. A, vol. 38, 1953, p. 58.

Database Beilstein, Beilstein Institute for Organic Chemistry, Frankfurt-Main, DE; XP002307103, Database Accession Nos. 22169, 3751528 (BRN's). & J. Am. Chem. Soc., vol. 40, 1980, p. 566.

Database Beilstein, Beilstein Institute for Organic Chemistry, Frankfurt-Main, DE; XP002307104, Database Accession Nos. 197306, 3795001 (BRN's), & Gazz. Chim. Ital., vol. 80, 1950, p. 456.

Database Chemcats 'Online!, Chemical Abstracts Service, Columbus, Ohio, US; XP002307105, retrieved from STN, Order No. 2022-2088. & "Interchim Intermediates" Jul. 9, 2002, Interchim, 213 Avenue Kennedy, BP 1140, Montlucon, Cedex, 03103, France.

Klunder et al.: "Novel Non-Nucleoside Inhibitors of HIV-1 Reverse Transcriptase. 2. Tricyclic Pyridobenzoxazepinones and Dibenzoxazephinones.", J. Med. Chem., vol. 35, 1992, pp. 1887-1897, XP002307085.

Traxler: "Tyrosine Kinase Inhibitors in Cancer Treatment (Part II)" Expert Opinion on Therapeutic Patents, Ashley Publications, GB, vol. 8, No. 12, 1998, pp. 1599-1625, XP001183544, ISSN: 1354-3776.

Showalter et al: "Tyrosine Kinase Inhibitors. 16. 6,5,6-Tricyclic Benzothieno [3,2-d]pyrimidines and Pyrimido[5,4-b]- and -[4,5-b]indoles as Potent Inhibitors of the Epidermal Growth Factor Receptor Tyrosine Kinase" Journal of Medicinal Chemistry, American Chemical Society. Washington, US, vol. 42, 1999, pp. 5464-5474, XP002210181, ISSN: 0022-2633.

International Search Report dated Dec. 9, 2004, for corresponding international application No. PCT?US2004/012729.

Dhanoa et al, "Serine Proteases-Directed Small Molecule Probe Libraries", Medicinal Chemistry Research, vol. 8, No. 4/5 (1998) pp. 187-205 (XP009016618) ISSN: 1054-2523.

Database Beilstein, Beilstein Crossfire Institut Zur Foerderung Der Chemischen Wissenschaften, DE; BRN 214943, BRN 214944, BRN 303350 (XP002378023).

Blankley et al, "Antihypertensive Activity of 6-Arylpyrido[2,3-d]pyrimidin-7-amine Derivatives. 2. 7-Acyl Amide Analogues", *Journal of Medicinal Chemistry*, vol. 26, No. 3, Mar. 1, 1983, pp. 403-411, ISSN: 0022-2623 (XP002000852).

Chan et al, "Halogen Substitution at the Isoxazole Ring Enhances the Activity of N-(Isoxazolyl)sulfonamide Endothelin Antagonists", *Bioorganic & Medicinal Chemistry Letters*, vol. 6, No. 20, 1996, pp. 2393-2398, ISSN: 0960-894X (XP002314441).

Contreras et al, "Aminopyridazines as Acetylcholinesterase Inhibitors", *Journal of Medicinal Chemistry*, vol. 42, No. 4, Feb. 25, 1999, pp. 730-741, ISSN: 0022-2623 (XP002353008).

Moffett et al, "Antiulcer Agents. p-Aminobenzamido Aromatic Compounds", *Journal of Medicinal Chemistry*, vol. 14, No. 10, Oct. 1971, pp. 963-968, ISSN: 0022-2623 (XP002057311).

Robert-Piessard et al, "Non-acidic Anti-inflammatory Compounds: Activity of N-(4,6-dimethyl-2-pyridinyl) Benzamides and Derivatives", *European Journal of Medicinal Chemistry*, vol. 25, No. 1, 1990, pp. 9-19, ISSN: 0223-5234 (XP001062115).

Seydel et al, " Quantitative Structure-Pharmacokinetic Relationships Derived on Antibacterial Sulfonamides in Rats and Its Comparison to Quantitative Structure-Activity Relationships", *Journal of Medicinal Chemistry*, vol. 23, No. 6, Jun. 1980, pp. 607-613, ISSN: 0022-2623 (XP002392659).

Stein et al, "Discovery and Structure-Activity Relationships of Sulfonamide $Et_A$-Selective Antagonists", *Journal of Medicinal Chemistry*, vol. 38, No. 8, 1995, pp. 1344-1354, ISSN: 0022-2623 (XP002314442).

Database Beilstein, Beilstein Crossfire Institut Zur Foerderung Der Chemischen Wissenschaften, DE; BRN 316474 1954 (XP0023922714).

Database Beilstein, Beilstein Crossfire Institut Zur Foerderung Der Chemischen Wissenschaften, DE; BRN 393777 1966 (XP002392715).

Database Beilstein, Beilstein Crossfire Institut Zur Foerderung Der Chemischen Wissenschaften, DE; BRN 5344832 1922 (XP002392716).

Database Beilstein, Beilstein Crossfire Institut Zur Foerderung Der Chemischen Wissenschaften, DE; BRN 7604813 1996 (XP002392717).

Database Beilstein, Beilstein Crossfire Institut Zur Foerderung Der Chemischen Wissenschaften, DE; BRN 8848189 2001 (XP002392718).

Database Beilstein, Beilstein Crossfire Institut Zur Foerderung Der Chemischen Wissenschaften, DE; BRN 7600437 1996 (XP002392719).

Database Beilstein, Beilstein Crossfire Institut Zur Foerderung Der Chemischen Wissenschaften, DE; BRN 5448817 1991 (XP002392720).

Database Beilstein, Beilstein Crossfire Institut Zur Foerderung Der Chemischen Wissenschaften, DE; BRN 6975717 1985 (XP002392721).

Database Beilstein, Beilstein Crossfire Institut Zur Foerderung Der Chemischen Wissenschaften, DE; BRN 7036362 1994 (XP002392722).

Database Beilstein, Beilstein Crossfire Institut Zur Foerderung Der Chemischen Wissenschaften, DE; BRN 410569 1971 (XP002392723).

Database Beilstein, Beilstein Crossfire Institut Zur Foerderung Der Chemischen Wissenschaften, DE; BRN 438575 1973 (XP002392724).

Database Beilstein, Beilstein Crossfire Institut Zur Foerderung Der Chemischen Wissenschaften, DE; BRN622512 1974 (XP002392725).

Database Beilstein, Beilstein Crossfire Institut Zur Foerderung Der Chemischen Wissenschaften, DE; BRN4209696 1990 (XP002392726).

Database Beilstein, Beilstein Crossfire Institut Zur Foerderung Der Chemischen Wissenschaften, DE; BRN 309332 1946 (XP002392727).

Database Beilstein, Beilstein Crossfire Institut Zur Foerderung Der Chemischen Wissenschaften, DE; BRN 253307 1959 (XP002392728).

Database Beilstein, Beilstein Crossfire Institut Zur Foerderung Der Chemischen Wissenschaften, DE; BRN308560 1948 (XP002392729).

Database CA. Chemical Abstracts Service. Vostrova, L.N. 'Nitrogen Heterocycles Based on Derivatives of Diimidazo [1,5-a;1',5'-d]pyrazine-5,10-diones' Database Accession No. 1983:126026. XP002401298. Abstract. Ukrainskii Khimicheskii Zhurnal (Russian Edition)(1982) 48(10)1074-7.

Database Chemcats. Chemical Abstracts Service. XP002401299. 'Enamine Screening Library' Jan. 24, 2006.

Dumas, J. 'Protein Kinase Inhibitors: Emerging Pharmacophores 1997-2000' Expert Opinion on Therapeutic Patents vol. 11 No. 3, pp. 405-429. XP002206851.

International Search Report re: PCT/US2005/038307 dated Oct. 19, 2006.

International Search Report re: PCT/US2006/014886 dated Nov. 2, 2006.

Beier et al, CA122:132943 (1995).

Freund et al, CA63;1170b (1982)

Snyder, Journal of Medicinal Chemistry (1967) 10(4):737-739.

* cited by examiner

C-FMS KINASE INHIBITORS

RELATIONSHIP TO OTHER APPLICATIONS AND PRIORITY CLAIM

This application is a continuation-in-part of U.S. Ser. No. 10/831,216, filed Apr. 26, 2004, now pending; which in turn claimed benefit under 35 U.S.C. § 119(e) to Provisional Application No. 60/465,204, filed Apr. 25, 2003.

FIELD OF THE INVENTION

The invention relates to novel compounds that function as protein tyrosine kinase inhibitors. More particularly, the invention relates to novel compounds that function as inhibitors of c-fms kinase.

BACKGROUND OF THE INVENTION

Protein kinases are enzymes that serve as key components of signal transduction pathways by catalyzing the transfer of the terminal phosphate from ATP to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. One embodiment of the invention is directed to the novel compounds of Formula I:

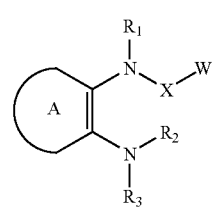

or a solvate, hydrate, tautomer or pharmaceutically acceptable salt thereof, wherein A is
  phenyl, naphthyl or biphenyl, each of which may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$; or a 5- to 7-membered mono- or a 8- to 10-membered bicyclic heteroaromatic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$;

$R_1$ is
  —H, aryl, —$COR_a$, —$COR_a$, —$COOR_a$, —$CONR_aR_b$, —$SO_2R_a$ or —$SO_2NR_aR_b$;

X is
—CO—, —C(=NH)—, —CS—, —CON($R_a$)—, —CS($NR_a$)—, —$SO_2$— or —$CR_aR_b$—;

$R_2$ and $R_3$ are independently
—H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$; and W is
phenyl, naphthyl or biphenyl, each of which may be optionally substituted with one or more of $C_{1-4}$ alkyl, amino, aminoalkyl, hydroxyalkyl, alkoxyalkyl, halogen, hydroxy, —$CF_3$, alkoxy, aryloxy, arylalkoxy, —$OCF_3$, —$COR_a$, —CN, —C(NH)$NH_2$, —$COOR_a$, —$CONR_aR_b$, —$NHCOR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

The compounds of Formulae I and II are especially potent inhibitors of the c-fms protein tyrosine kinase. The compounds of Formula III are expected to exhibit similar inhibitory potencies.

The invention also relates to methods of inhibiting protein tyrosine kinase activity in a mammal by administration of a therapeutically effective amount of at least one compound of Formula I, II or III.

DETAILED DESCRIPTION OF THE INVENTION

The invention is directed to the novel compounds of Formula I:

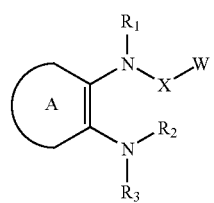

I or a solvate, hydrate, tautomer or pharmaceutically acceptable salt thereof, wherein A is
phenyl, naphthyl or biphenyl, each of which may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; or a 5- to 7-membered mono- or a 8- to 10-membered bicyclic heteroaromatic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$;

$R_1$ is
—H, aryl, —$COR_a$, —$COR_a$, —$COOR_a$, —$CONR_aR_b$, —$SO_2R_a$ or —$SO_2NR_aR_b$;

X is
—CO—, —C(=NH)—, —CS—, —CON($R_a$)—, —CS($NR_a$)—, —$SO_2$— or —$CR_aR_b$—;

$R_2$ and $R_3$ are independently
—H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$; and W is
phenyl, naphthyl or biphenyl, each of which may be optionally substituted with one or more of $C_{1-4}$ alkyl, amino, aminoalkyl, hydroxyalkyl, alkoxyalkyl, halogen, hydroxy, —$CF_3$, alkoxy, aryloxy, arylalkoxy, —$OCF_3$, —$COR_a$, —CN, —C(NH)$NH_2$, —$COOR_a$, —$CONR_aR_b$, —$NHCOR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Preferred compounds of Formula I are those wherein

A is phenyl;

$R_1$ is —H; and $R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Particularly preferred compounds of Formula I are those wherein

A is phenyl;

$R_1$ is —H;

$R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$; and W is a phenyl, furan, thiophene, isoxazole, pyrrole, oxazole, thiazole, imidazole, pyrazole, isothiazole, triazole, pyridine, pyridazine, pyrimidine, pyrazine or triazine ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$C(NH)NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

The most preferred compounds of Formula I include, but are not limited to, 5-cyano-furan-2-carboxylic acid [2-(4-acetylamino-piperidin-1-yl)-phenyl]-amide, 5-cyano-1H-pyrrole-2-carboxylic acid (2-piperidin-1-yl-phenyl)-amide, 5-cyano-furan-2-carboxylic acid (4-methoxy-2-piperidin-1-yl-phenyl)-amide, 5-cyano-furan-2-carboxylic acid (4-imidazol-1-yl-2-piperidin-1-yl-phenyl)-amide, 5-cyano-furan-2-carboxylic acid (4-dimethylamino-2-piperidin-1-yl-phenyl)-amide, 5-cyano-furan-2-carboxylic acid [2-(4,4-difluoro-piperidin-1-yl)-phenyl]-amide, 5-cyano-furan-2-carboxylic acid (4-ethoxy-2-piperidin-1-yl-phenyl)-amide, 5-cyano-furan-2-carboxylic acid (3-chloro-2-piperidin-1-yl-phenyl)-amide, 5-cyano-furan-2-carboxylic acid (3-methyl-2-piperidin-1-yl-phenyl)-amide, 5-cyano-furan-2-carboxylic acid (2-piperidin-1-yl-4-pyrazol-1-yl-phenyl)-amide, 5-cyano-furan-2-carboxylic acid [4-(acetyl-methyl-amino)-2-piperidin-1-yl-phenyl]-amide,5-cyano-furan-2-carboxylic acid (4-acetylamino-2-piperidin-1-yl-phenyl)-amide, 5-cyano-furan-2-carboxylic acid [2-(4-methyl-piperidin-1-yl)-4-pyridin-4-yl-phenyl]-amide bis(trifluoroacetic acid salt), 3H-imidazole-4-carboxylic acid (2-piperidin-1-yl-phenyl)-amide bis(trifluoroacetic acid salt), or 5-cyano-1H-imidazole-2-carboxylic acid (2-piperidin-1-yl-phenyl)-amide trifluoroacetic acid salt, and pharmaceutically acceptable salts thereof.

The invention also relates to methods of inhibiting protein tyrosine kinase activity in a mammal by administration of a therapeutically effective amount of at least one compound of Formula. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

1. Definitions

The term "alkyl" refers to both linear and branched chain radicals of up to 12 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Alkyl substituents may optionally be present on the ring. Examples include cyclopropyl, 1,1-dimethyl cyclobutyl, 1,2,3-trimethylcyclopentyl, cyclohexyl and cyclohexenyl.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl and imidazolinyl.

The term "heterocyclylalkyl" refers to a $C_{1-6}$ alkyl group containing a heterocyclyl substituent. Examples include dihydropyranylethyl and 2-morpholinylpropyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "heteroaromatic" or "heteroaryl" refers to 5- to 7-membered mono- or 8- to 10-membered bicyclic aromatic ring systems, any ring of which may contain from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroaralkyl" refers to a $C_{1-6}$ alkyl group having a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "heteroaralkyl" refers to a $C_{1-6}$ alkyl group containing a heteroaryl substituent. Examples include furylmethyl and pyridylpropyl.

The term "aryloxy" refers to an oxygen atom bound to an aryl substituent. Examples include phenoxy and benzyloxy.

The term "arylalkoxy" refers to an alkoxy group bound to an aryl substituent. Examples include phenylmethyl ether.

The term "acyl" refers to the group $—C(O)R_a$, where $R_a$ is alkyl, aryl, aralkyl, heteroaryl and heteroaralkyl. An "acylating agent" adds the $—C(O)R_a$ group to a molecule.

The term "sulfonyl" refers to the group $—S(O)_2R_a$, where $R_a$ is hydrogen, alkyl, cycloalkyl, haloalkyl, aryl, aralkyl, heteroaryl and heteroaralkyl. A "sulfonylating agent" adds the $—S(O)_2R_a$ group to a molecule.

II. Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, breast cancer, colon cancer, stomach cancer, hairy cell leukemia and non-small lung carcinoma. In one embodiment of the invention, an effective amount of at least one compound of Formula I is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I. Examples of diseases that may be effectively treated include glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

The compounds of Formula I may be prepared by either solid phase support methodology or by solution-phase synthesis. Exemplary synthetic routes for generating amides of the invention are described below.

Scheme 1

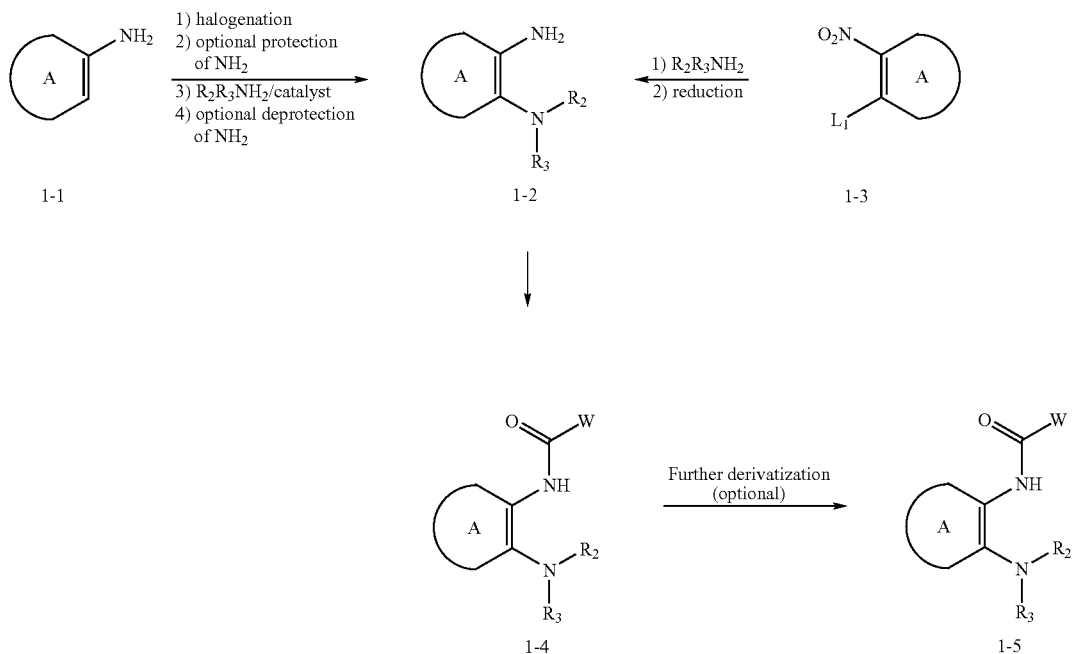

Scheme 1 illustrates general methodology for the preparation of compounds of Formula I.

Compounds of Formula 1-2 can be obtained by nucleophilic aromatic substitution on compounds of Formula 1-3 (where $L_1$ is a leaving group such as a halogen, preferably fluoro or chloro) with amines $R_2R_3NH$ followed by reduction of the nitro group. Nucleophilic aromatic displacements can be performed in the presence of a suitable base such as excess $R_2R_3NH$, triethylamine ($NEt_3$) or $K_2CO_3$ in a suitable solvent such as dimethylformamide (DMF). Nitro reductions can be performed according to standard synthetic methodologies (for a review, see M. Hudlicky, Reductions in Organic Chemistry, Wiley, N.Y. (1984)) and include preferred methods such as palladium-catalyzed hydrogenolysis or treatment with iron (0) and $NH_4Cl$ (see, for example, S. Mitsumori, et al, *J. Med. Chem.*, 46: 2436-45 (2003)).

Alternatively compounds of Formula 1-2 can be obtained by ortho-halogenation (preferably bromination) of amino compounds of Formula 1-1 followed by metal-catalyzed aminations with $R_2R_3NH$. (For reviews, see: S. L. Buchwald, et al, *Top. Curr. Chem.*, 219:131-209 (2001) and J. F. Hartwig in "*Organopalladium Chemistry for Organic Synthesis*," Wiley Interscience, NY (2002) and examples therein.) Catalysts suitable for aminations include metal complexes and salts of palladium and copper as described below and in the aforementioned references. The $NH_2$ group may be optionally protected prior to the coupling using a number of protecting groups such as tert-butoxycarbonyl (BOC) (see, for example, M. C. Harris, et al, Org. Lett., 4:2885-8 (2002).) (For examples of amine protecting groups and their use, see Theodora W. Greene and Peter G. M. Wuts, John Wiley and Sons, Inc., NY (1991)). The preferred conditions for bromination are N-bromosuccinimide (NBS) in a suitable solvent such as N,N-dimethylformamide (DMF), dichloromethane (DCM) or acetonitrile. Metal-catalyzed aminations can be performed according to standard methodology, preferably in the presence of a palladium catalyst such as $Pd_2(dba)_3$ or $Pd(OAc)_2$, a ligand such as BINAP or preferably 2-diphenylphoshino-2'-(N,N-dimethylamino)biphenyl, a base such as $Cs_2CO_3$, and a suitable solvent such as toluene, dioxane or DME. The protecting group, if present, would then be removed at this point using suitable reagents, preferably trifluoroacetic acid in DCM if the protecting group was a BOC.

Compounds of Formula 1-4 can be prepared by reaction of compounds of Formula 1-2 with carboxylic acids WCOOH according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters $WCO_2Rq$ (where Rq is a leaving group such as pentafluorophenyl or N-succinimide). The preferred reaction conditions for coupling with WCOOH are: when W is a furan, oxalyl chloride in DCM with DMF as a catalyst to form the acid chloride WCOCl and then coupling in the presence of a trialkylamine such as N,N-diisopropylethylamine (DIEA); when W is a pyrrole, 1-(3-dimethylaminopropyl)-3-carbodiimide hydrochloride (EDCI) and 1-hydroxybenzotriazole (HOBt); and when W is an imidazole, the preferred conditions are bromotri(pyrrolidino)phosphonium hexafluorophosphate (PyBroP) and DIEA in DCM.

It is understood that the optional substitution present in Formula I may be present in the starting materials 1-1 or 1-3 and, in such cases, would be carried through the synthesis outlined in Scheme 1. Alternatively various substituents on compounds of Formula I may be introduced in a number of ways described below to provide the optional substitution listed for Formula I. For example, leaving groups present on compounds of Formula 1-1 or 1-3, can be substituted before or at any step during Scheme 1. When such leaving groups (preferably fluoro or chloro) are activated by the nitro group of Formula 1-3 for nucleophilic attack, they can undergo direct nucleophilic aromatic substitution by ammonia and azide anion or by amines, alcohols, thiols and other nucleophiles in the presence of a suitable base such as K$_2$CO$_3$, DIEA or NEt$_3$. When the leaving group is suitable for metal-catalyzed couplings (preferably bromo or trifluoromethanesulfonyloxy), a number of cross-coupling reactions (such as Suzuki or Stille reactions) may be performed to introduce aryl, heteroaryl, alkenyl or cycloalkenyl groups (for reviews, see N. Miyaura, A. Suzuki, *Chem. Rev.*, 95:2457 (1995), J. K. Stille, *Angew. Chem, Int. Ed. Engl.*, 25: 508024 (1986) and A. Suzuki in Metal-Catalyzed Coupling Reactions, F. Deiderich, P. Stang, Eds., Wiley-VCH, Weinheim (1988)). Metal-catalyzed cross-couplings (preferably Suzuki reactions using a boronic acid or boronic ester) can be performed according to standard methodology, preferably in the presence of a palladium catalyst such as tetrakistriphenylphosphine Pd$^0$ (Pd (PPh$_3$)$_4$), an aqueous base such aq. Na$_2$CO$_3$, and a suitable solvent such as toluene, ethanol, DME, or DMF. Other metal-catalyzed coupling reactions that can be employed include aromatic and heteroaromatic amination and amidation (for reviews, see references for amination chemistry cited above for conversion of Formulas 1-1 to 1-2.)

In some cases, the initial substituents formed can be further derivatized as described below to provide the final substitution of Formula I.

Finally it is understood that substituents on compounds of Formula 1-4 may be further derivatized to provide compounds of Formula 1-5. Protecting groups on compounds of Formula 1-4 can be removed according to standard synthetic methodologies (see Theodora W. Greene and Peter G. M. Wuts, John Wiley and Sons, Inc., NY (1991)) and can be then subjected to further derivatization. Examples of further derivatization of compounds of 1-4 to provide compounds of Formulae 1-5 include, but are not limited to: when compounds of Formula 1-4 contain a primary or secondary amine, the amine may be reacted with aldehydes or ketones in the presence of a reducing agent such as sodium triacetoxyborohydride (see Abdel-Magid reference above) to reductively alkylate the amine; with acid chlorides or carboxylic acids and an amide bond forming reagent as described above to form amides; with sulfonyl chlorides to form sulfonamides; with isocyanates or carbamyl chlorides to form ureas; with aryl or heteroaryl halides in the presence of a palladium catalyst as described above (see Buchwald and Hartwig references above) to attach aryl and heteroaryl groups to the amines. In addition, when compounds of Formulae 1-4 contain an aryl or heteroaryl halide (preferably bromide) or an aryl or heteroaryl trifluoromethanesulfonyloxy group, these compounds may be further subjected to metal-catalyzed reactions with boronic acids (for example, Suzuki or Stille couplings as described above) to attach aryl or heteroaryl groups, or with amines, alcohols or thiols (Buchwald- or Hartwig-type couplings, see Buchwald and Hartwig references above) to attach various amino, alkoxy, aryloxy, alkylthio or arylthio groups. When compounds of Formulae 1-4 contain a cyano group, this group may be hydrolyzed to amides or acids under acid or basic conditions. The resulting acids may the coupled to amines to form amides using the methology described above. Basic amines may be oxidized to N-oxides and conversely N-oxides may be reduced to basic amines. When compounds of Formula 1-4 contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperoxybenzoic acid(MCPBA) or by treatment with NaIO$_4$ (see, for example, J. Regan, et al, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919).

EXAMPLE 1

5-Cyano-furan-2-carboxylic acid [2-(4-acetylamino-piperidin-1-yl)-phenyl]-amide a) 5-Cyano-furan-2-carboxylic acid

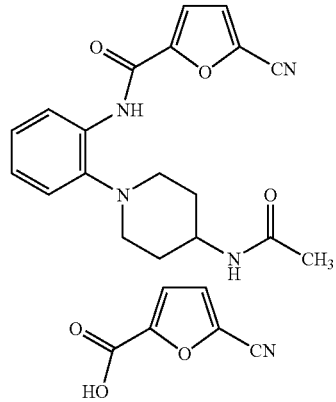

To 2.8 g of 2-formyl-5-furancarboxylic acid (20 mmol) and 2.7 g of hydroxylamine hydrochloride (40 mmol) under Ar was added and dry pyridine (50 mL). The mixture was heated to 85° C., acetic anhydride (40 mL) was added and the mixture was stirred for 3 h. After cooling to 60° C., water (250 mL) was added and the mixture was stirred at RT for 70 h. The mixture was acidified to pH 2 with concentrated hydrochloric acid and extracted with 3:1 dichloromethane-isopropanol (8×100 mL). The combined organic layers were washed with water (100 mL), brine (100 mL), dried over anh sodium sulfate and concentrated in vacuo to afford the title compound as a tan solid (1.26 g, 46%). $^1$H-NMR (CD$_3$OD; 400 MHz): δ 14.05 (br s, 1H), 7.74 (d, 1H, J=3.8 Hz), 7.42 (d, 1H, J=3.8 Hz).

b) 4-Acetylamino-piperidinium acetate

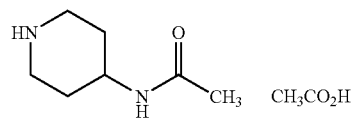

To a solution of 4-aminopiperidine (524 μL, 5.00 mmol) in diethyl ether (20 mL) was added a solution of acetic anhydride (567 μL, 0.600 mmol)) in diethyl ether (20 mL) over 10 minutes and the resulting mixture was stirred for 1 h at RT. The solid was collected on a Buchner funnel, washed with diethyl ether (50 mL), and dried under vacuo to give 867 mg (86%) of the title compound as a white solid. $^1$H-NMR (400 MHz, CDCl$_3$): δ 7.82 (d, 1H, J=10.5 Hz), 4.20-4.16 (m, 1H), 3.78-3.71 (m, 2H), 3.45 (br s, 1H), 3.09 (m, 1H), 2.69 (m, 1H), 1.98 (s, 3H), 1.79 (s, 3H), 1.78-1.69 (m, 2H), 1.28-1.13 (m, 2H).

c) N-[1-(2-Nitro-phenyl)-piperidin-4-yl]-acetamide

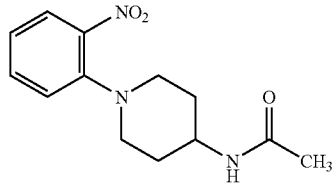

To a flask was added 4-acetylamino-piperidinium acetate (as prepared in the previous step) (800 mg, 4.00 mmol), DMF (40 mL), 2-fluoro-1-nitrobenzene (422 µL, 4.00 mmol), triethylamine (836 µL, 6.00 mmol) and the mixture stirred at RT for 17 h. The solvents were removed in vacuo and the residue was purified by silica gel preparative TLC eluting with dichloromethane/hexane/acetonitrile (47.5/47.5/5 v:v:v) yielded 55 mg (5%) of the title compound as a crystalline orange solid. $^1$H-NMR (400 MHz, CDCl$_3$): δ 8.18 (m, 1H), 8.09 (br d, 1H, J=7.2 Hz), 7.45 (m, 1H), 6.88 (m, 1H), 6.67 (m, 1H), 4.38 (m, 1H), 3.86-3.74 (m, 1H), 3.32 (m, 1H), 3.07 (m, 1H), 2.14 (s, 3H), 1.67-1.52 (m, 2H).

d) N-[1-(2-Amino-phenyl)-piperidin-4-yl]-acetamide

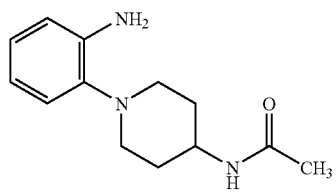

To a solution of N-[1-(2-nitro-phenyl)-piperidin-4-yl]-acetamide (as prepared in the previous step) (55 mg, 0.21 mmol) in methanol (10 mL) was added 10% palladium on carbon (50 mg) and the mixture stirred at RT for 1 h under hydrogen (1 atm). The mixture was filtered through a short column of Celite and the solvent removed in vacuo to yield 48 mg (100%) of the title compound as a purple solid. $^1$H-NMR (400 MHz, CDCl$_3$): δ 6.82-6.67 (m, 4H), 4.44 (m, 1H), 3.78 (m, 1H), 3.35 (br s, 2H), 3.21 (m, 1H), 2.91 (m, 1H), 2.11 (s, 3H), 2.12-2.04 (m, 2H), 1.75 (br s, 1H), 1.41 (m, 2H). LC-MS (ESI, m/z): Calcd. for C$_{13}$H$_{20}$N$_3$O, 234.2 (M+H); found: 234.0.

e) 5-Cyano-furan-2-carboxylic acid [2-(4-acetylamino-piperidin-1-yl)-phenyl]-amide To a solution of 5-cyano-furan-2-carboxylic acid (as prepared in step (a), this example, 58 mg, 0.42 mmol) in dichloromethane (10 mL) was added DMF (50 µL), and oxalyl chloride (40 µL, 0.46 mmol) and the mixture stirred for 1 h at RT. The solvents were removed in vacuo, the residue was then taken up into dichloromethane (5 mL). This solution was added to a stirred solution of N-[1-(2-amino-phenyl)-piperidin-4-yl]-acetamide (as prepared in the previous step) (48 mg/0.21 mmol) and DIEA (110 µL, 0.63 mmol) in dichloromethane (5 mL). The mixture was stirred for 17 h at RT and poured into satd aq sodium bicarbonate (50 mL), and extracted with dichloromethane (3×30 mL). The organic layers were washed with water (20 mL), brine (20 mL), dried over Na$_2$SO$_4$ and concentrated in vacuo. Purification of the resulting residue by silica gel preparative TLC eluting with 10% methanol in dichloromethane yielded 23 mg (31%) of the title compound as a brown solid. $^1$H-NMR (400 MHz, CDCl$_3$): δ 8.41 (br s, 1H), 8.36 (d, 1H, J=8.4 Hz), 7.66-7.64 (m, 2H), 7.42-7.36 (m, 2H), 7.29-7.20 (m, 3H), 7.23 (d, 1H, J=3.7 Hz), 7.20 (dd, 1H, J=1.2, 7.5 Hz), 6.71 (dd, 1H, J=0.7, 3.4 Hz), 6.65 (m, 1H). LC-MS (ESI, m/z): Calcd. for C$_{19}$H$_{21}$N$_4$O$_3$, 353.2 (M+H); found: 353.0.

EXAMPLE 2

5-Cyano-1H-pyrrole-2-carboxylic acid (2-piperidin-1-yl-phenyl)-amide

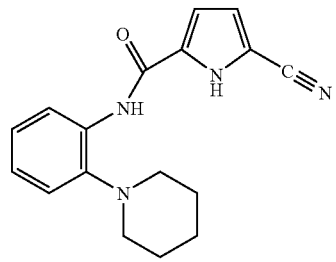

a) 5-Formyl-1H-pyrrole-2-carboxylic acid ethyl ester

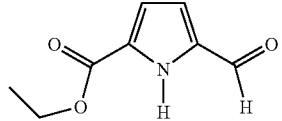

To DMF (1.3 mL, 17 mmol) cooled to 5-10° C. was added phosphorous oxychloride (1.5 mL) dropwise and the mixture was diluted with 1,2-dichloroethane (5 mL). The flask was then cooled to −10° C. and ethyl pyrrole-2-carboxylate (2.00 g, 14.4 mmol) in 1,2-dichloroethane (5 mL) was added dropwise over 5 min. The mixture was heated to reflux for 15 min, cooled to RT and ethyl acetate (15 mL), water (20 mL), and satd aq sodium bicarbonate (70 mL) were added. The layers were separated and the aqueous layer was extracted with diethyl ether (3×20 mL). The combined organic layers were washed with saturated sodium carbonate (50 mL), dried (Na$_2$SO$_4$) and the solvents were removed in vacuo. The resulting solid was purified by column chromatography on silica gel (300 g), eluting with 30% ethyl acetate in hexane to yield 1.0 g (42%) of the title compound as a pale yellow crystalline solid. $^1$H-NMR (400 MHz, CDCl$_3$): δ 9.89 (br s, 1H), 9.67 (s, 1H), 6.95 (d, 1H, J=4.1 Hz), 6.94 (d, 1H, J=4.1 Hz), 4.38 (q, 2H, J=7.1 Hz), 1.39 (t, 3H, J=7.1).

b) 5-(Hydroxyimino-methyl)-1H-pyrrole-2-carboxylic acid ethyl ester

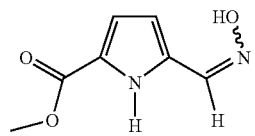

A mixture of 5-formyl-1H-pyrrole-2-carboxylic acid ethyl ester (as prepared in the previous step, 300 mg, 1.80 mmol), hydroxylamine hydrochloride (560 mg, 8.10 mmol), ethanol (10 mL), sodium acetate (1.10 g, 13.4 mmol) and water (10 mL) was stirred at 90° C. for 30 min. The solvents were removed in vacuo and the solid was collected on a Buchner funnel and washed with water (10 mL) to yield 226 mg (69%) of the title compound as a white solid: LC-MS (ESI, m/z): Calcd. for $C_8H_{11}N_2O_3$, 183.1 (M+H); found: 183.0.

c) 5-Cyano-1H-pyrrole-2-carboxylic acid ethyl ester

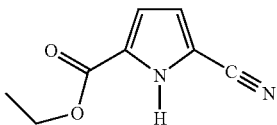

A solution of 5-(hydroxyimino-methyl)-1H-pyrrole-2-carboxylic acid ethyl ester (as prepared in the previous step) (500 mg, 2.75 mmol) in acetic anhydride (5 mL) was stirred at 140° C. for 2 h. The cooled mixture was quenched with ice and then dichloromethane was added and the mixture was made basic with solid sodium bicarbonate. The layers were separated, the organic layer was washed with saturated sodium bicarbonate (2×10 mL), water (2×10 mL), then dried over $Na_2SO_4$. The solvent was removed in vacuo to yield 260 mg (58%) of the title compound as a light brown crystalline solid. $^1$H-NMR (400 MHz, $CDCl_3$): δ 10.45 (br s, 1H), 6.89 (m, 1H), 6.83 (m, 1H), 4.42 (q, 2H, J=7.2 Hz), 1.40 (t, 3H, J=7.1 Hz).

d) 5-Cyano-1H-pyrrole-2-carboxylic acid

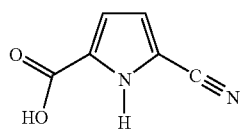

To 260 mg of 5-cyano-1H-pyrrole-2-carboxylic acid ethyl ester (as prepared in the previous step) (1.59 mmol) in ethanol (6 mL) was added $_1$M aq sodium hydroxide (3.00 mL, 3.00 mmol) and the mixture was stirred at 80° C. for 2.5 h. The solvent was removed in vacuo, and the resulting solution was acidified to pH 3 with concentrated hydrochloric acid. The solid was collected on a filter and washed with water (1 mL) and dried under high vacuum to yield the title compound as a light tan solid which was used without further purification in the following step.

e) 5-Cyano-1H-pyrrole-2-carboxylic acid (2-piperidin-1-yl-phenyl)-amide

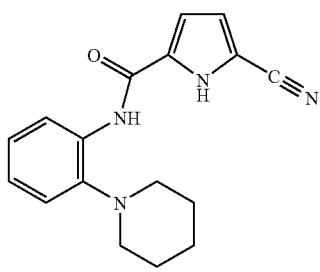

To 24.5 mg (0.180 mmol) 5-cyano-1H-pyrrole-2-carboxylic acid (as prepared in the previous step) in dichloromethane (10 mL) was added 53 mg (0.28 mmol) of 1-(3-dimethylaminopropyl)-3-ethylcarbodiimide hydrochloride (EDCI), hydroxybenzotriazole (HOBt, 30 mg, 0.22 mmol), and 2-piperidinoaniline (38 mg, 0.22 mmol) and the mixture stirred for 6.5 h at RT. The mixture was poured into brine (50 mL) and extracted with dichloromethane (3×20 mL). The organic layers were washed with brine (20 mL), dried over $Na_2SO_4$ and the solvent was removed in vacuo. Purification of the resulting residue by silica gel preparative TLC eluting with 30% ethyl acetate in hexane yielded 24 mg (42%) of the title compound as a brown solid. $^1$H-NMR (400 MHz, $CDCl_3$): δ 11.90 and 10.45 (br s, 1H, rotomers), 9.60 and 9.38 (s, 1H, rotomers), 8.60 and 8.47 (d, 1H, J=7.9 Hz, rotomers), 7.29-6.74 (m, 5H), 2.85 (m, 4H), 1.78-1.68 (m, 6H). LC-MS (ESI, m/z): Calcd. for $C_{17}H_{19}N_4O$, 295.2 (M+H); found: 295.2.

EXAMPLE 3

5-Cyano-furan-2-carboxylic acid (4-methoxy-2-piperidin-1-yl-phenyl)-amide

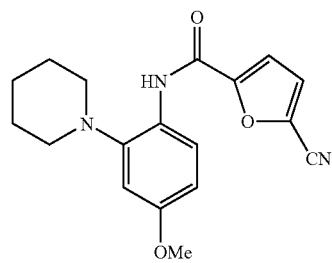

a) 1-(5-Chloro-2-nitro-phenyl)-piperidine

To a cooled (0° C.) solution of 1.75 g (10.0 mmol) of 4-chloro-2-fluoronitrobenzene in 15 mL of EtOH was added 2.97 mL (30.0 mmol) of piperidine dropwise over 5 min. The solution stirred at 0° C. for 10 min and then at 23° C. for 30 min. The mixture was poured into water (225 mL) and extracted with EtOAc (2×30 mL). The combined extracts were washed with saturated aq $NaHCO_3$ and brine (30 mL each) and then dried ($Na_2SO_4$). Concentration afforded 2.33 g (97%) of the title compound as an orange oil which crystallized on standing: Mass spectrum (ESI, m/z): Calcd. for $C_{11}H_{13}ClN_2O_2$, 241.1 (M+H), found 241.1.

b) 1-(5-Methoxy-2-nitro-phenyl)-piperidine

To 1-(5-chloro-2-nitro-phenyl)-piperidine (197 mg, 0.810 mmol) in 1.5 mL of DMF was added 4 mL of 0.5 M NaOMe in MeOH (2.5 eq). The resultant solution was heated at 60° C. overnight, then at 90° C. for 24 h. The reaction was diluted with EtOAc (50 mL) and washed with water (50 mL), dried ($Na_2SO_4$) and concentrated in vacuo. Purification by preparative TLC (20% EtOAc-hexane) gave 80 mg (41%) of the title compound, along with 80 mg (40%) of recovered starting material. $^1$H-NMR ($CDCl_3$; 400 MHz): δ 7.95 (d, 1H, J=9.1 Hz), 6.51 (d, 1H, J=2.6 Hz), 6.46 (dd, 1H, J=2.6, 9.1 Hz), 3.87 (s, 3H), 3.01-3.04 (m, 4H), 1.72-1.78 (m, 4H), 1.60-1.64 (m, 2H).

c) 4-Methoxy-2-piperidin-1-yl-phenylamine 1-(5-methoxy-2-nitro-phenyl)-piperidine (80 mg, 0.33 mmol, as prepared in the previous step) was stirred with 55 mg of 5% Pd—C in MeOH (4 mL) under $H_2$ balloon pressure for 2 h. The reaction was filtered through Celite and concentrated in vacuo to afford 67 mg (98%) of the title compound as a reddish solid, which was used immediately without further purification. Mass spectrum (ESI, m/z): Calcd. for $C_{12}H_{18}N_2O$, 207.1 (M+H), found 207.2.

d) 5-Cyano-furan-2-carboxylic acid (4-methoxy-2-piperidin-1-yl-phenyl)-amide

Using a procedure similar to Example 1, step (e), 5-cyano-furan-2-carbonyl chloride (66 mg, 0.43 mmol) was allowed to react with 4-methoxy-2-piperidin-1-yl-phenylamine (67 mg, 0.32 mmol, as prepared in the previous step) in the presence of DIEA (164 μL, 0.940 mmol) for 2 h to afford 62 mg (60%) of the title compound as a yellow solid. $^1$H-NMR (CDCl$_3$; 400 MHz): δ 9.49 (br s, 1H) 8.35 (d, 1H, J=8.9 Hz), 7.27-7.22 (m, 1H), 6.76 (d, 1H, J=2.7 Hz), 6.71 (dd, 1H, J=2.8, 8.9 Hz), 3.81 (s, 3H), 2.85-2.83 (m, 4H), 1.84-1.78 (m, 4H), 1.66-1.65 (m, 2H); Mass spectrum (ESI, m/z): Calcd. for C$_{18}$H$_{19}$N$_3$O$_3$, 326.1 (M+H), found 326.1.

EXAMPLE 4

5-Cyano-furan-2-carboxylic acid (4-imidazol-1-yl-2-piperidin-1-yl-phenyl)-amide

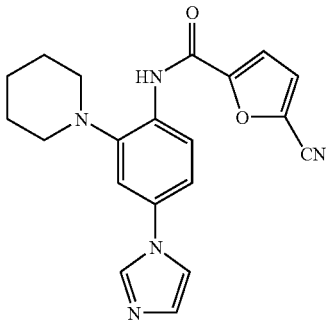

a) 1-(5-Imidazol-1-yl-2-nitro-phenyl)-piperidine

To 1-(5-chloro-2-nitro-phenyl)-piperidine (184 mg, 0.760 mmol, as prepared in Example 3, step (a)) and imidazole (67.8 mg, 0.99 mmol) in 3 mL of DMSO was added KOH (64 mg, 1.1 mmol). The reaction was heated to 90° C. overnight. The dark solution was poured into 40 mL of water and extracted with EtOAc (2×50 mL). The combined organic layers were washed with water (50 mL), dried (Na$_2$SO$_4$) and concentrated in vacuo to give 190 mg (92%) of the title compound as a yellow solid. Mass spectrum (ESI, m/z): Calcd. for C$_{14}$H$_{16}$N$_4$O$_2$, 273.1 (M+H), found 273.1.

b) 4-Imidazol-1-yl-2-piperidin-1-yl-phenylamine

To 1-(5-imidazol-1-yl-2-nitro-phenyl)-piperidine (117 mg, 0.430 mmol, as prepared in the previous step) in 3 mL of THF was added 6.5 mL of 10% TiCl$_3$ in H$_2$O dropwise over 3 min. After 10 min, the reaction was extracted with 20 mL of EtOAc, and the organic layer was discarded. The aqueous layer was basified with 10M NaOH to pH>9, then extracted with EtOAc (3×20 mL). The combined organic layers were washed with brine (20 mL), dried (Na$_2$SO$_4$), and concentrated in vacuo to afford 74 mg (66%) of the title compound as a light brown solid. Mass spectrum (ESI, m/z): Calcd. for C$_{14}$H$_{18}$N$_4$, 243.1 (M+H), found 243.2;

c) 5-Cyano-furan-2-carboxylic acid (4-imidazol-1-yl-2-piperidin-1-yl-phenyl)-amide Using a procedure similar to Example 3, step (d), 4-imidazol-1-yl-2-piperidin-1-yl-phenylamine (69 mg, 0.28 mmol, as prepared in the previous step) was allowed to react with 5-cyano-furan-2-carbonyl chloride (56 mg, 0.36 mmol) in the presence of DIEA (138 μL, 0.790 mmol) to afford 44.9 mg (44%) of the title compound as a yellow solid. $^1$H-NMR (CDCl$_3$; 400 MHz): δ 9.65 (br s, 1H), 8.57 (d, 1H, J=9.3 Hz), 7.84 (s, 1H), 7.34 (d, 1H, J=3.7 Hz), 7.28-7.27 (m, 2H), 7.22-7.20 (m, 3H), 2.93-2.90 (m, 4H), 1.88-1.85 (m, 4H), 1.72 (br s, 2H); Mass spectrum (ESI, m/z): Calcd. for C$_{20}$H$_{19}$N$_5$O$_2$, 362.1 (M+H), found 362.2.

EXAMPLE 5

5-Cyano-furan-2-carboxylic acid (4-dimethylamino-2-piperidin-1-yl-phenyl)-amide

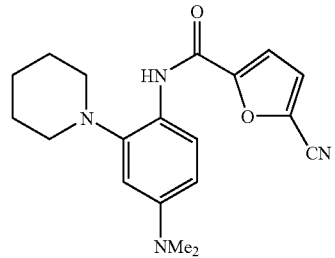

a) 1-(5-Fluoro-2-nitro-phenyl)-piperidine

To a solution of 2,4-difluoronitrobenzene (2.09 g, 13.1 mmol) in EtOH (10 mL) at ambient temperature was added piperidine (3.35 g, 39.4 mmol) dropwise. The reaction was allowed to stir overnight and concentrated in vacuo. The residue was dissolved in EtOAc (100 mL), washed with water (2×100 mL), dried (Na$_2$SO$_4$) and concentrated in vacuo. Purification by silica gel column chromatography afforded 1.10 (37%) of the title compound as an oil. Mass spectrum (ESI, m/z): Calcd. for C$_{11}$H$_{13}$FN$_2$O$_2$, 225.1 (M+H), found 225.1.

b) Dimethyl-(4-nitro-3-piperidin-1-yl-phenyl)-amine

To a solution of 1-(5-fluoro-2-nitro-phenyl)-piperidine (294 mg, 1.31 mmol, as prepared in the previous step) in 8 mL EtOH-DMF (v/v) was added NaCN (128 mg, 2.6 mmol). The reaction was heated to 130° C. in a sealed tube for 24 h. The reaction was diluted with EtOAc (50 mL) and washed with water (2×50 mL). Chromatography (50% EtOAc-hexane) of the crude product afforded 88 mg (27%) the title compound as well as 78 mg (24%) (1-(5-ethoxy-2-nitro-phenyl)-piperidine as yellow solids. Mass spectrum (ESI, m/z): Calcd. for C$_{13}$H$_{19}$N$_3$O$_2$, 250.1 (M+H), found 250.0.

c) 4-N,N-Dimethyl-2-piperidin-1-yl-benzene-1,4-diamine

Using a procedure similar to Example 3, step (c), dimethyl-(4-nitro-3-piperidin-1-yl-phenyl)-amine (100 mg, 0.4 mmol, as prepared in the previous step) was stirred with 80 mg 5% Pd—C in 5 mL MeOH under H$_2$ to afford 89 mg (100%) of the title compound as an oil, which was used immediately without further purification. Mass spectrum (ESI, m/z) calcd. for C$_{13}$H$_{21}$N$_3$, 220.1 (M+H), found 220.1.

d) 5-Cyano-furan-2-carboxylic acid (4-dimethylamino-2-piperidin-1-yl-phenyl)-amide Using a procedure similar to Example 3, step (d), 4-N,N-dimethyl-2-piperidin-1-yl-benzene-1,4-diamine (89 mg, 0.4 mmol, as prepared in the previous step) was allowed to react with 5-cyano-furan-2-carbonyl chloride (236 mg, 1.5 mmol) in the presence of DIEA (0.15 mL, 0.88 mmol) to afford 84.7 mg (63%) of the title compound as a yellow powder. $^1$H-NMR (CDCl$_3$, 400 MHz): δ 9.50 (br s, 1H), 8.29 (d, 1H, J=8.9 Hz), 7.21-7.24 (m, 2H), 6.58 (d, 1H, J=2.7 Hz), 6.54 (dd, 1H, J=2.8, 9.0 Hz), 2.95 (s, 6H), 2.84-2.87 (m, 4H), 1.78-1.82 (m, 4H), 1.65 (br s, 2H); Mass spectrum (ESI, m/z): Calcd. for $C_{19}H_{22}N_4O_2$, 339.1 (M+H), found 339.1.

EXAMPLE 6

5-Cyano-furan-2-carboxylic acid [2-(4,4-difluoro-piperidin-1-yl)-phenyl]-amide

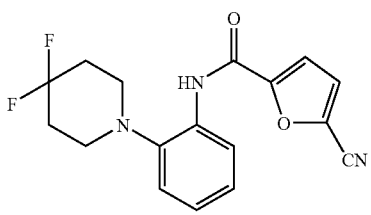

a) 4,4-Difluoro-1-(2-nitro-phenyl)-piperidine

To a mixture of 2-fluoro-nitrobenzene (116 mg, 0.82 mmol) and 4-difluoropiperidine hydrochloride salt (142 mg, 0.9 mmol) in 3 mL of DMF was added $Cs_2CO_3$ (731 mg, 2.2 mmol). The reaction was heated to 80° C. for 4 h. At this time the mixture was poured into water (20 mL) and then extracted with $CHCl_3$ (2×50 mL). The organic layers were dried ($Na_2SO_4$) and concentrated in vacuo to give 128 mg (64%) of a yellow solid and used without further purification. Mass spectrum (ESI, m/z): Calcd. for $C_{11}H_{12}F_2N_2O_2$, 243.0 (M+H), found 243.2.

b) 2-(4,4-Difluoro-piperidin-1-yl)-phenylamine

Using a procedure similar to Example 3, step (c), 4,4-difluoro-1-(2-nitro-phenyl)-piperidine (128 mg, 0.520 mmol, as prepared in the previous step) was stirred with 80 mg 5% Pd—C in 4 mL of MeOH under $H_2$ to afford 76 mg (69%) of the title compound as a dark oil, which was used immediately due to apparent instability. Mass spectrum (ESI, m/z): Calcd. for $C_{11}H_{14}F_2N_2$, 213.1 (M+H), found 213.1.

c) 5-Cyano-furan-2-carboxylic acid [2-(4,4-difluoro-piperidin-1-yl)-phenyl]-amide Using a procedure similar to Example 3, step (d), 2-(4,4-difluoro-piperidin-1-yl)-phenylamine (76 mg, 0.35 mmol) was allowed to react with 5-cyano-furan-2-carbonyl chloride (62 mg, 0.40 mmol) in the presence of DIEA (134 µL, 0.770 mmol) to afford 42 mg (36%) of the title compound as a tan solid. $^1$H-NMR (CDCl$_3$; 400 MHz): δ 9.60 (br s, 1H), 8.44 (dd, 1H, J=1.3, 8.1 Hz) 7.32 (d, 1H, J=3.8 Hz), 7.27-7.21 (m, 3H), 7.18-7.13 (m, 1H), 3.07-3.04 (m, 4H), 2.29-2.21 (m, 4H); Mass spectrum (ESI, m/z): Calcd. for $C_{17}H_{15}F_2N_3O_2$, 332.1 (M+H), found 332.1.

EXAMPLE 7

5-Cyano-furan-2-carboxylic acid (4-ethoxy-2-piperidin-1-yl-phenyl)-amide

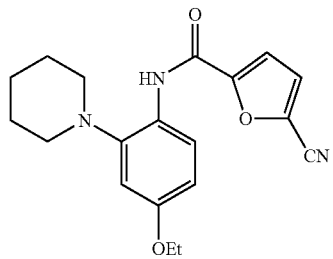

a) 1-(5-Ethoxy-2-nitro-phenyl)-piperidine

To 1-(5-chloro-2-nitro-phenyl)-piperidine (197 mg, 0.810 mmol, as prepared in Example 3, step (a)) in 1.5 mL of DMF was added 4 mL of 0.5 M NaOEt in EtOH (1.94 mmol). The resultant solution was heated at 90° C. for 24 h. The reaction was diluted with EtOAc (50 mL) and washed with water (50 mL), dried ($Na_2SO_4$) and concentrated in vacuo. Purification by preparative tlc (20% EtOAc-hexane) gave 110 mg (54%) of the title compound. Mass spectrum (ESI, m/z): Calcd. for $C_{13}H_{18}N_2O_3$, 251.1 (M+H), found 251.1.

b) 4-Ethoxy-2-piperidin-1-yl-phenylamine

Using a procedure similar to Example 3, step (c), 1-(5-ethoxy-2-nitro-phenyl)-piperidine (78 mg, 0.31 mmol, as prepared in the previous step) was stirred with 42 mg of 5% Pd—C under $H_2$ to afford 64 mg (94%) of the title compound which was used immediately without further purification. Mass spectrum (ESI, m/z): Calcd. for $C_{13}H_{20}N_2O$, 221.1 (M+H), found 221.1.

c) 5-Cyano-furan-2-carboxylic acid (4-ethoxy-2-piperidin-1-yl-phenyl)-amide

Using a procedure similar to Example 3, step (d), 4-ethoxy-2-piperidin-1-yl-phenylamine (64 mg, 0.29 mmol, as prepared in the previous step) was allowed to react with 5-cyano-furan-2-carbonyl chloride (66.6 mg, 0.430 mmol) in the presence of DIEA (111 µL, 0.63 mmol) to afford 53 mg (54%) of the title compound as a light yellow solid. $^1$H-NMR (CDCl$_3$, 400 MHz): δ 9.49 (br s, 1H), 8.32 (d, 1H, J=8.9 Hz), 7.25 (d, 1H, J=2.7 Hz), 7.22 (d, 1H, J=2.8 Hz), 6.77 (d, 1H, J=2.8 Hz), 6.67 (dd, 1H, J=2.8, 8.9 Hz), 2.82 (m, 4H), 4.02 (q, 2H, J=7.0 Hz), 2.82 (m, 4H), 1.80-1.82 (m, 4H), 1.64 (br s, 2H), 1.41 (t, 3H, J=7.0 Hz); Mass spectrum (ESI, m/z): Calcd. for $C_{19}H_{21}N_3O_3$, 340.1 (M+H), found 340.1.

EXAMPLE 8

5-Cyano-furan-2-carboxylic acid (3-chloro-2-piperidin-1-yl-phenyl)-amide

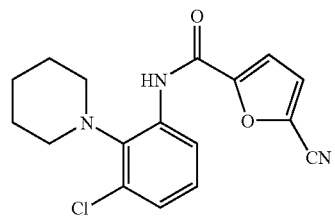

a) 1-(2-Chloro-6-nitro-phenyl)-piperidine

To a flask containing 2,3-dichloronitrobenzene (387 mg, 2.01 mmol) was added 3 mL of piperidine, and the result was heated to 80° C. overnight. The reaction was diluted with EtOAc (30 mL), washed with water (2×30 mL), dried ($Na_2SO_4$) and concentrated in vacuo. Purification by preparative tlc (20% EtOAc-hexane) yielded 320 mg (66%) of the title compound as a yellow solid. $^1$H-NMR ($CDCl_3$; 400 MHz): δ 7.56-7.50 (m, 2H), 7.04 (t, 1H, J=8.1 Hz), 3.04 (br s, 4H), 1.69 (br s, 4H), 1.59 (br s obscured by water, 2H).

b) 3-Chloro-2-piperidin-1-yl-phenylamine

Using a procedure similar to Example 3, step (c), 1-(2-chloro-6-nitro-phenyl)-piperidine (79 mg, 0.32 mmol, as prepared in the previous step) was stirred with 44 mg of 5% Pd—C under $H_2$ for 1 h 30 min to afford 54 mg (80%) of the title compound, contaminated with the des-chloro derivative, which was used immediately without further purification. Mass spectrum (ESI, m/z): Calcd. for $C_{11}H_{15}ClN_2$, 211.0 (M+H), found 211.1.

c) 5-Cyano-furan-2-carboxylic acid (3-chloro-2-piperidin-1-yl-phenyl)-amide

Using a procedure similar to Example 3, step (d), 3-chloro-2-piperidin-1-yl-phenylamine (54 mg, 0.25 mmol, as prepared in the previous step) was allowed to react with 5-cyano-furan-2-carbonyl chloride (55.8 mg, 0.360 mmol) in the presence of DIEA (95 μL, 0.55 mmol) to afford 8.4 mg (10%) of the title compound as a yellow solid. $^1$H-NMR ($CDCl_3$; 400 MHz): δ 10.70 (br s, 1H), 8.42 (dd, 1H, J=1.4, 8.1 Hz), 7.30 (dd, J=1.5, 3.7 Hz), 7.24 (d, 1H, J=3.7 Hz), 7.17 (t, 1H, J=8.1 Hz), 7.07 (dd, 1H, J=1.4, 8.1 Hz), 3.58-3.52 (m, 2H), 2.85-2.82 (m, 2H), 2.02-1.99 (m, 1H), 1.89-1.72 (m, 4H), 1.52-1.38 (m, 1H), Mass spectrum (ESI, m/z): Calcd. for $C_{17}H_{16}ClN_3O_2$, 330.0 (M+H), found 330.1.

EXAMPLE 9

5-Cyano-furan-2-carboxylic acid (3-methyl-2-piperidin-1-yl-phenyl)-amide

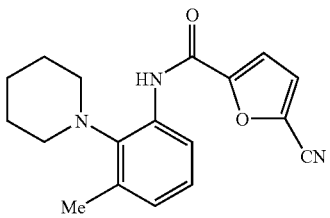

a) 1-(2-Methyl-6-nitro-phenyl)-piperidine

Using a procedure similar to Example 8, step (a), 2-chloro-3-methylnitrobenzene (264 mg, 1.53 mmol) was heated to 110° C. overnight in 3 mL of piperidine to afford 128 mg (35%) of the title compound and an undetermined amount of starting material. $^1$H-NMR ($CDCl_3$; 400 MHz): δ 7.41-7.34 (m, 2H), 7.02 (t, 1H, J=7.7 Hz), 2.96-2.93 (m, 4H), 2.36 (s, 3H), 1.65 (br s, 6H).

b) 3-Methyl-2-piperidin-1-yl-phenylamine

Using a procedure similar to Example 3, step (c), 1-(2-methyl-6-nitro-phenyl)-piperidine (74 mg, 0.38 mmol, as prepared in the previous step) was stirred with 5% Pd—C (50 mg) under $H_2$ to afford 66 mg (91%) of the title compound as an oil. Mass spectrum (ESI, m/z): Calcd. for $C_{12}H_{18}N_2$, 191.1 (M+H), found 191.1.

c) 5-Cyano-furan-2-carboxylic acid (3-methyl-2-piperidin-1-yl-phenyl)-amide

Using a procedure similar to example 3, step (d), 3-methyl-2-piperidin-1-yl-phenylamine (68 mg, 0.35 mmol, as prepared in the previous step) was allowed to react with 5-cyano-furan-2-carbonyl chloride (65 mg, 0.42 mmol) in the presence of DIEA (134 μL, 0.77 mmol) to afford 13 mg (12%) of the title compound as a waxy yellow solid. $^1$H-NMR ($CDCl_3$, 400 MHz): δ 10.7 (br s, 1H), 8.33 (d, 1H, J=8.0 Hz), 7.27 (d, 1H, J=3.7 Hz), 7.22 (dd, 1H, 3.7 Hz), 7.12 (t, 1H, J=7.9 Hz), 6.87 (dd, 1H, J=0.7, 7.7 Hz), 3.22-3.28 (m, 2H), 2.88-2.91 (m, 1H), 2.41 (s, 3H), 2.01-2.04 (m, 1H), 1.80-1.86 (m, 4H), 1.43-1.47 (m, 1H); Mass spectrum (ESI, m/z): Calcd. for $C_{18}H_{19}N_3O_2$, 310.1 (M+H), found 310.2.

EXAMPLE 10

5-Cyano-furan-2-carboxylic acid (2-piperidin-1-yl-4-pyrazol-1-yl-phenyl)-amide

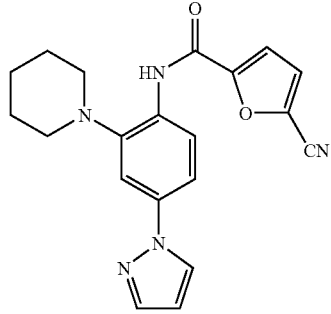

a) 1-(2-Nitro-5-pyrazol-1-yl-phenyl)-piperidine

Using a procedure similar to Example 4, step (a), a solution of 1-(5-fluoro-2-nitro-phenyl)-piperidine (98 mg, 0.43 mmol, as prepared in Example 5, step (a)), pyrazole (67.8 mg, 0.600 mmol), and NaOH (22.4 mg, 0.560 mmol) were heated in 3 mL of DMSO overnight to afford 100 mg (85%) the title compound as a yellow solid. Mass spectrum (ESI, m/z): Calcd. for $C_{14}H_{16}N_4O_2$, 273.1 (M+H), found 273.1.

b) 5-Cyano-furan-2-carboxylic acid (2-piperidin-1-yl-4-pyrazol-1-yl-phenyl)-amide Using a procedure similar to Example 4, step (b), 1-(2-nitro-5-pyrazol-1-yl-phenyl)-piperidine (100 mg, 0.31 mmol, as prepared in the previous step) was allowed to react with $TiCl_3$ (1.80 mL, 2.94 mmol) in 3 mL of THF to afford 72 mg (94%) of 2-piperidin-1-yl-4-pyrazol-1-yl-phenylamine, which was allowed to react in a manner similar to Example 3, step (d), with 5-cyano-furan-2-carbonyl chloride (67.5 mg, 0.43 mmol) in the presence of DIEA (111 μL, 0.6 mmol) to afford 52.7 mg (47%) of the title compound as a light yellow solid. $^1$H-NMR (CDCl$_3$; 400 MHz): δ 9.67 (s, 1H), 8.50 (d, 1H, J=8.8 Hz), 7.90 (d, 1H, J=2.4 Hz), 7.71 (d, 1H, J=1.5 Hz), 7.65 (d, 1H, J=2.4 Hz), 7.37 (dd, 1H, J=2.5, 8.8 Hz), 7.29 (d, 1H, J=3.8 Hz), 7.23 (d, 1H, J=3.7 Hz), 6.46-6.45 (m, 1H), 2.92-2.89 (m, 4H), 1.85-1.80 (m, 4H), 1.66 (br s, 2H); Mass spectrum (ESI, m/z): Calcd. for C$_{20}$H$_{19}$N$_5$O$_2$ 362.1 (M+H), found 362.2.

EXAMPLE 11

5-Cyano-furan-2-carboxylic acid [4-(acetyl-methyl-amino)-2-piperidin-1-yl-phenyl]-amide

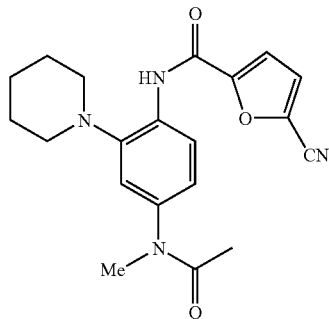

a) N-Methyl-(4-nitro-3-piperidin-1-yl-phenyl)-amine

A solution of 1-(5-fluoro-2-nitro-phenyl)-piperidine (200 mg, 0.89 mmol, as prepared in Example 5, step (a)) in 4 mL of 2M methylamine in MeOH was heated in a sealed tube for 12 h at 80° C. solvent under vacuum afforded methyl-(4-nitro-3-piperidin-1-yl-phenyl)-amine (209 mg, 100%). Mass spectrum (ESI, m/z): Calcd. for C$_{12}$H$_{17}$N$_3$O$_2$, 236.1 (M+H), found 236.1.

b) N-Methyl-N-(4-nitro-3-piperidin-1-yl-phenyl)-acetamide

To a solution of methyl-(4-nitro-3-piperidin-1-yl-phenyl)-amine (80 mg, 0.34 mmol, as prepared in the previous step) and triethylamine (118 μL, 0.850 mmol)) in 4 mL of CH$_2$Cl$_2$ was added acetic anhydride (320 μL, 3.40 mmol) via microsyringe and the reaction was allowed to stir overnight. At this time it was diluted with CHCl$_3$ (50 mL), washed with satd aq NaHCO$_3$ (2×50 mL), and dried (Na$_2$SO$_4$). Concentration of the solvent in vacuo and purification of the crude material using preparative TLC (4% MeOH—CHCl$_3$) afforded 67 mg (71%) of the title compound as an oil. Mass spectrum (ESI, m/z): Calcd. for C$_{14}$H$_{19}$N$_3$O$_3$, 278.1 (M+H), found 278.1.

c) 5-Cyano-furan-2-carboxylic acid [4-(acetyl-methyl-amino)-2-piperidin-1-yl-phenyl]-amide Using a procedure similar to Example 3, step (c), N-methyl-N-(4-nitro-3-piperidin-1-yl-phenyl)-acetamide (67 mg, 0.24 mmol, as prepared in the previous step) was stirred with 5% Pd—C (45 mg) under H$_2$ to afford N-(4-amino-3-piperidin-1-yl-phenyl)-N-methyl-acetamide which was used immediately. Using a procedure similar to Example 3, step (d) this was coupled to 5-cyano-furan-2-carbonyl chloride (52 mg, 0.33 mmol) in the presence of DIEA (107 μL, 0.55 mmol) to afford 7.3 mg (8%) of the title compound as a waxy solid. $^1$H-NMR (CDCl$_3$; 400 MHz): δ 9.66 (s, 1H), 8.48 (d, 1H, J=9.2 Hz), 7.34 (d, 1H, J=3.7 Hz), 7.26 (d, 1H, J=3.3 Hz), 7.03-7.01 (m, 2H), 3.27 (s, 3H,), 2.88-2.86 (m, 4H), 1.90 (s, 3H), 1.88-1.82 (m, 4H), 1.63 (br s, 2H); Mass spectrum (ESI, m/z): Calcd. for C$_{20}$H$_{22}$N$_4$O$_3$, 367.1 (M+1), found 367.2.

EXAMPLE 12

5-Cyano-furan-2-carboxylic acid (4-acetylamino-2-piperidin-1-yl-phenyl)-amide

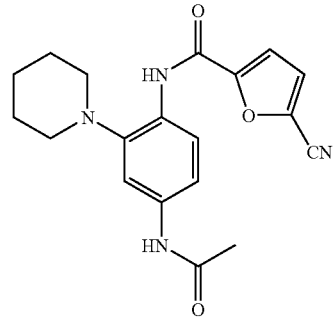

a) Methyl-(4-nitro-3-piperidin-1-yl-phenyl)-amine

A solution of 1-(5-fluoro-2-nitro-phenyl)-piperidine (200 mg, 0.89 mmol) in 4 mL of 2M methylamine in MeOH was heated in a sealed tube for 12 h at 80° C. Removal of the solvent under vacuum afforded methyl-(4-nitro-3-piperidin-1-yl-phenyl)-amine (209 mg, 100%). Mass spectrum (ESI, m/z): Calcd. for C$_{12}$H$_{17}$N$_3$O$_2$, 236.1 (M+H), found 236.1.

b) N-(4-Amino-3-piperidin-1-yl-phenyl)-acetamide

4-Nitro-3-piperidin-1-yl-phenylamine (64 mg, 0.28 mmol, as prepared in the previous step) and DIEA (122 μL, 0.700 mmol) in 4 mL of CH$_2$Cl$_2$ was treated with acetyl chloride (28 μL, 0.40 mmol). The reaction was stirred for 1 h, diluted with CH$_2$Cl$_2$ (25 mL), washed with water (50 mL), and dried (Na$_2$SO$_4$). Concentration of the solvent in vacuo afforded 51 mg (78%) of N-(4-nitro-3-piperidin-1-yl-phenyl)-acetamide. Using a procedure similar to Example 3, step (c), 4-nitro-3-piperidin-1-yl-phenylamine (51 mg, 0.21 mmol) was stirred with 5% Pd—C (35 mg) under H$_2$ to afford 40 mg (61%) of the title compound as a dark semi-solid. Mass spectrum (ESI, m/z): Calcd. for C$_{13}$H$_{19}$N$_3$O, 234.1 (M+H), found 234.2.

c) 5-Cyano-furan-2-carboxylic acid (4-acetylamino-2-piperidin-1-yl-phenyl)-amide Using a procedure similar to Example 3, step (d), N-(4-amino-3-piperidin-1-yl-phenyl)-acetamide (40 mg, 0.17 mmol, as prepared in the previous step) was allowed to react with 5-cyano-furan-2-carbonyl chloride (27 mg, 0.17 mmol) in the presence of DIEA (65 μL, 0.37 mmol) to afford 23 mg (38%) of the title compound as a yellow solid. $^1$H-NMR (CDCl$_3$; 400 MHz): δ 9.64 (s, 1H),), 8.36 (d, 1H, J=8.5 Hz), 7.70 (br s, 1H), 7.27 (br s, 1H), 7.22 (d, 1H, J=3.8 Hz), 7.14 (br s, 1H), 7.02 (dd, 1H, J=6.6, 8.9 Hz), 2.85 (br s, 4H), 2.18 (s, 3H), 1.80 (br s, 4H), 1.65 (br s, 2H); Mass spectrum (ESI, m/z): Calcd. for C$_{19}$H$_{20}$N$_4$O$_3$, 353.1 (M+H), found 353.2.

EXAMPLE 13

5-Cyano-furan-2-carboxylic acid [2-(4-methyl-piperidin-1-yl)-4-pyridin-4-yl-phenyl]-amide bis(trifluoroacetic acid salt).

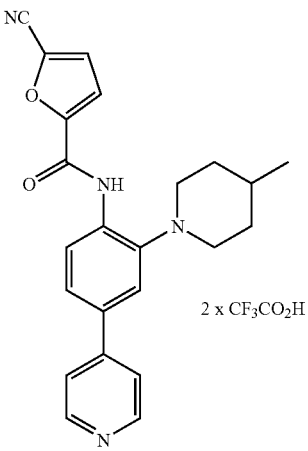

a) 1-(5-Bromo-2-nitro-phenyl)-4-methyl-piperidine

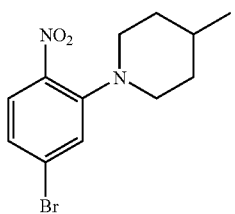

A solution of 4-bromo-2-fluoro-phenylamine (3.00 g, 15.8 mmol) in 15 mL of DCM is added drop wise to a suspension of 3-chloroperoxybenzoic acid (19 g, 57-86%) in 200 mL of DCM at −10° C. and the mixture is allowed to attain RT and stirred for 10 h. The reaction is then washed with saturated aqueous NaHCO$_3$ (2×150 mL) and brine (100 mL), and the organic layer dried over Na$_2$SO$_4$ and evaporated. MeOH (10 mL) was then added to the crude residue to precipitate a white solid that was removed by filtration and the filtrate was concentrated to give 4-bromo-2-fluoro-1-nitro-benzene. This product was dissolved in 100 mL of DCM, cooled to 0° C., and 4-methylpiperidine (5.00 g, 50.8 mmol) was added and the solution was stirred for 10 h at RT. The reaction was diluted with 100 mL of DCM, washed with brine (3×100 mL), and the organic layer dried over Na$_2$SO$_4$ and concentrated. The crude oil was purified by elution from a 20-g solid phase extraction (SPE) cartridge (silica) with 50% DCM/hexanes to give 3.4 g (72%) of the title compound as a yellow oil: Mass spectrum (ESI, m/z): Calcd. for C$_{12}$H$_{15}$BrN$_2$O$_2$, 299.0 (M+H), found 299.1.

b) 4-Bromo-2-(4-methyl-piperidin-1-yl)-phenylamine

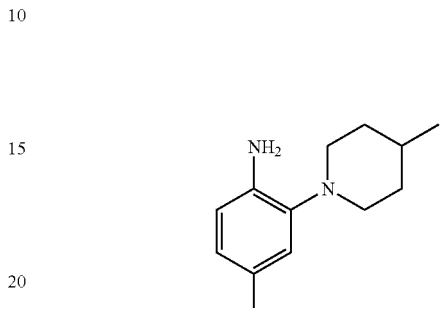

A flask charged with 1-(5-bromo-2-nitro-phenyl)-4-methyl-piperidine (1.0 g, 3.3 mmol) (as prepared in the previous step), ammonium chloride (1.8 g, 33 mmol), iron powder (0.93 g, 16 mmol), EtOH (12 mL) and water (6 mL) was heated at 80° C. for 1 h. The reaction was filtered though Celite, concentrated and eluted from a 20-g SPE cartridge (silica) with 100% DCM to give 0.80 g (91%) of the title compound as a yellow oil. Mass spectrum (ESI, m/z): Calcd. for C$_{12}$H$_{17}$BrN$_2$, 269.1/271.1 (M+H), found 269.1/271.1.

c) 5-Cyano-furan-2-carboxylic acid [4-bromo-2-(4-methyl-piperidin-1-yl)-phenyl]-amde

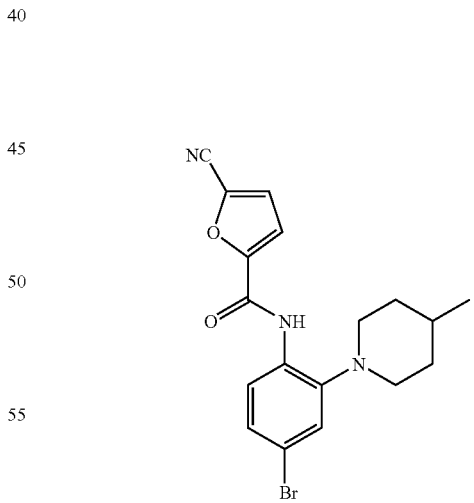

The title compound was obtained by coupling 4-bromo-2-(4-methyl-piperidin-1-yl)-phenylamine (as prepared in the previous step) to 5-cyano-furan-2-carboxylic acid (as prepared in Example 1, step (a)) according to the procedure in Example 1, step (e). Mass spectrum (ESI, m/z): Calcd. for C$_{18}$H$_{18}$BrN$_3$O$_2$, 388.1/390.1 (M+H), found 388.1/390.1.

d) Furan-2,5-dicarboxylic acid 2-amide 5-{[2-(4-methyl-piperidin-1-yl)-4-pyridin-4-yl-phnyl]-amide

EXAMPLE 14

3H-Imidazole-4-carboxylic acid (2-piperidin-1-yl-phenyl)-amide bis(trifluoroacetic acid salt).

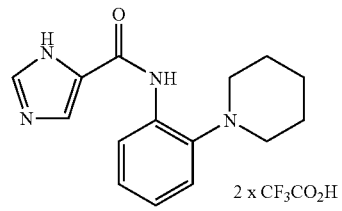

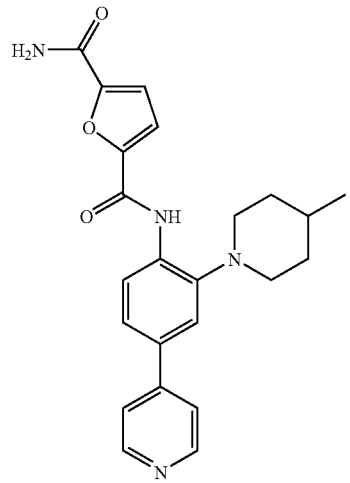

a) 1-(2-Trimethylsilanyl-ethoxymethyl)-1H-imidazole-4-carboxyate sodium salt

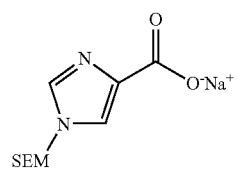

A flask charged with 1H-imidazole-4-carboxylic acid methyl ester (0.29 g, 2.3 mmol), $K_2CO_3$ (0.60 g, 4.3 mmol), SEM-Cl (0.45 mL, 2.5 mmol) and DMF (5 mL) was heated for 12 h at 80° C. The reaction was diluted with EtOAc (20 mL) and washed with water (20 mL) and brine (20 mL) and the organic layer dried over $MgSO_4$ and concentrated. The residue was purified by elution from a 20-g SPE cartridge (silica) with 5% MeOH/DCM to give 0.50 g (85%) of 1-(2-trimethylsilanyl-ethoxymethyl)-1H-imidazole-4-carboxylic acid methyl ester. This compound was stirred overnight at RT in MeOH (3.0 mL) and 1N NaOH (1.9 mL) and then concentrated to give 0.43 g (70%) of the title compound as a white solid. Mass spectrum (ESI), m/z): Calcd. for $C_{10}H_{18}N_2O_3Si$, 243.1 (M+H), found 243.1.

b) 1-(2-Trimethylsilanyl-ethoxymethyl)-1H-imidazole-4-carboxylic acid (2-piperidin-1-yl-phenyl)-amide A flask was charged with 5-cyano-furan-2-carboxylic acid [4-bromo-2-(4-methyl-piperidin-1-yl)-phenyl]-amide (0.048 g, 0.12 mmol) (as prepared in the previous step), pyridyl-4-boronic acid (0.022 g, 0.18 mmol), Pd(PPh$_3$)$_4$ (0.014 g, 10 mol %), 2M Na$_2$CO$_3$ (0.5 mL), and DMF (1 mL) and heated for 12 h at 75° C. The reaction was diluted with EtOAc (10 mL) and washed with brine (2×10 mL). The organic layer was dried (Na$_2$SO$_4$) and concentrated and the title product (0.40 g, 83%) eluted from a 10-g SPE cartridge (silica) with 100% EtOAc. Mass spectrum (ESI, m/z): Calcd. for $C_{23}H_{24}N_4O_2$, 405.2 (M+H), found 405.2.

e) 5-Cyano-furan-2-carboxylic acid [2-(4-methyl-piperidin-1-yl)-4-pyridin-4-yl-phenyl]-amide bis(trifluoroacetic Acid Salt)

A flask charged with furan-2,5-dicarboxylic acid 2-amide 5-{[2-(4-methyl-piperidin-1-yl)-4-pyridin-4-yl-phenyl]-amide (0.040 g, 0.10 mmol) (as prepared in the previous step), pyridine (0.025 mL, 0.30 mmol), p-toluenesulfonyl chloride (0.030 g, 0.15 mmol), and DMF (1 mL) was heated for 2 h at 100° C. The reaction was diluted with EtOAc (10 mL) and washed with satd NaHCO$_3$ (2×10 mL) and brine (10 mL). The organic layer was dried (Na$_2$SO$_4$) and concentrated and the residue was purified by RP-HPLC (C18), eluting with 40-70% CH$_3$CN in 0.1% TFA/H$_2$O over 10 min to give 0.021 g (34%) the title compound. 1H-NMR (400 MHz, CD$_3$OD): δ 8.84 (d, 2H), 8.59 (d, 1H), 8.42 (d, 2H), 7.94 (d, 1H), 7.86 (dd, 1H), 7.56 (d, 1H), 7.44 (d, 1H), 3.12 (m, 2H), 2.96. (m, 2H), 1.96 (m, 2H), 1.60 (m, 3H), 1.14 (d, 3H). Mass spectrum (ESI): Calcd. for $C_{23}H_{22}N_4O_2$, 387.2 (M+H), found 387.2.

A flask was charged with 1-(2-trimethylsilanyl-ethoxymethyl)-1H-imidazole-4-carboxylate sodium salt (70 mg, 0.26 mmol) (as prepared in the previous step), 2-piperidin-1-yl-phenylamine (36 mg, 0.20 mmol), EDCI (60 g, 0.31 mmol), DMAP (25 mg, 0.20 mmol), and DMF (1 mL) and stirred for 3 h at RT. The reaction was diluted with EtOAc (10 mL) and washed with brine (2×10 mL), and the organic layer was dried over $Na_2SO_4$ and then concentrated. The title compound was eluted from a 5-g SPE cartridge (silica) with 30% EtOAc/hexane to give 80 mg (97%) of a white solid. Mass spectrum (ESI, m/z): Calcd. for $C_{21}H_{32}N_4O_2Si$, 401.2 (M+H), found 401.1.

c) 3H-Imidazole-4-carboxylic acid (2-piperidin-1-yl-phenyl)-amide bis(trifluoroacetic acid salt).

To a solution of 1-(2-trimethylsilanyl-ethoxymethyl)-1H-imidazole-4-carboxylic acid (2-piperidin-1-yl-phenyl)-amide (80 mg, 0.20 mmol) (as prepared in the previous step) in EtOH (0.6 mL) was added 6N HCl (0.3 mL) and the mixture heated to 75° C. for 6 h. The mixture was concentrated and the title compound was purified by RP-HPLC (C18) eluting with 5-30% $CH_3CN$ in 0.1% $TFA/H_2O$ over 10 min to give 35 mg (35%) of a white solid. $^1$H-NMR (400 MHz, DMSO-$d_6$): δ 10.00 (s, 1H), 8.28 (m, 1H), 8.16 (m, 1H), 7.98 (s, 1H), 7.22 (m, 1H), 7.10 (m, 2H), 2.84 (m, 4H), 1.80 (m, 4H), 1.58 (m, 2H). Mass spectrum (ESI, m/z): Calcd. for $C_{15}H_{18}N_4O$, 271.2 (M+H), found 271.2.

EXAMPLE 15

5-Cyano-1H-imidazole-2-carboxylic acid (2-piperidin-1-yl-phenyl)-amide trifluoroacetic acid Salt

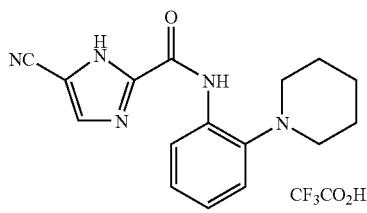

a) 1-(2-Trimethylsilanyl-ethoxymethyl)-1H-imidazole-4-carbonitrile

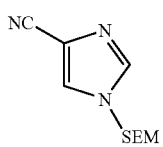

A flask charged with imidazole-4-carbonitrile (0.50 g, 5.2 mmol) (Synthesis, 677 (2003)) 2-(trimethylsilyl)ethoxymethyl chloride (SEMCl) (0.95 mL, 5.3 mmol), $K_2CO_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over $MgSO_4$. The crude product was eluted from a 20-g SPE cartridge (silica) with 30% EtOAc/hexane to give 0.80 g (70%) of the title compound as a colorless oil. Mass spectrum (CI ($CH_4$), m/z) Calcd. for $C_{10}H_{17}N_3OSi$, 224.1 (M+H), found 224.1.

b) 2-Bromo-1-(2-trimethylsilanyl-ethoxymethyl)-1H-imidazole-4-carbonitrile

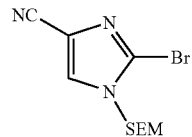

To a solution of 1-(2-trimethylsilanyl-ethoxymethyl)-1H-imidazole-4-carbonitrile (0.70 g, 3.1 mmol) (as prepared in the previous step) in $CCl_4$ (10 mL) was added NBS (0.61 g, 3.4 mmol) and AIBN (2 mg, catalytic), and the mixture heated at 60° C. for 4 h. The reaction was diluted with EtOAc (30 mL) and washed with $NaHCO_3$ (2×30 mL) and brine (30 mL) and the organic layer was dried over $Na_2SO_4$ and then concentrated. The title compound was eluted from a 20-g SPE cartridge (silica) with 30% EtOAc/hexane to give 0.73 g (77%) of a yellow solid. Mass spectrum (CI($CH_4$), m/z) Calcd. for $C_{10}H_{16}BrN_3OSi$, 302.0/304.0 (M+H), found 302.1/304.1.

c) 4-Cyano-1-(2-trimethylsilanyl-ethoxymethyl)-1H-imidazole-2-carboxylic acid ethyl ester

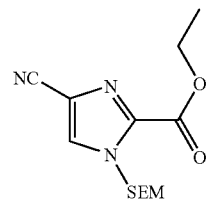

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added dropwise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq $NH_4Cl$, diluted with EtOAc (20 mL) and washed with brine (2×20 mL), and the organic layer was dried over $Na_2SO_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for $C_{13}H_{21}N_3O_3Si$, 296.1 (M+H), found 296.1.

d) 4-Cyano-1-(2-trimethylsilanyl-ethoxymethyl)-1H-imidazole-2-carboxylate potassium salt

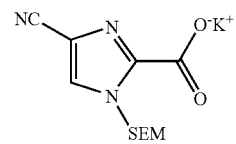

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.20 mL) and the reaction was stirred for 10 min and then concentrated to give 0.40 g (100%) of the title compound as a yellow solid. $^1$H-NMR (400 MHz, CD$_3$OD): δ 7.98 (s, 1H), 5.92 (s, 2H), 3.62 (m, 2H), 0.94 (m, 2H), 0.00 (s, 9H). Mass spectrum (ESI-neg, m/z) Calcd. for C$_{11}$H$_{17}$N$_3$O$_3$Si, 266.1 (M−H), found 266.0.

e) 5-Cyano-1H-imidazole-2-carboxylic acid (2-piperidin-1-yl-phenyl)-amide trifluoroacetic acid salt The title compound was prepared by coupling 4-cyano-1-(2-trimethylsilanyl-ethoxymethyl)-1H-imidazole-2-carboxylate potassium salt (as prepared in the previous step) and 2-piperidin-1-yl-phenylamine according to the procedure in Example 14, step (b) followed by SEM deprotection according to the procedure in Example 14, step (c). The title compound was purified by RP-HPLC (C18), eluting with 10-70% CH$_3$CN in 0.1% TFA/H$_2$O over 15 min. 1H-NMR (400 MHz, CD$_3$OD): δ 8.38 (m, 1H), 8.06 (s, 1H), 7.32 (m, 1H), 7.18 (m, 2H), 2.92 (m, 4H), 1.92 (m, 4H), 1.72 (m, 2H). Mass spectrum (ESI, m/z): Calcd. for C$_{16}$H$_{17}$N$_5$O, 296.1 (M+H), found 296.1.

The invention claimed is:

1. A compound of Formula I:

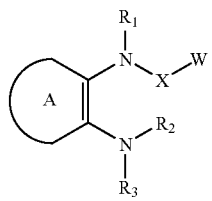

I or a solvate, hydrate, tautomer or pharmaceutically acceptable salt thereof, wherein A is phenyl, which may be optionally substituted with one or more of —C$_{1-6}$ alkyl, amino, aminoalkyl, hydroxyalkyl, alkoxyalkyl, sulfonamidoalkyl, guanidinoalkyl, heteroaryl, halogen, hydroxy, —CF$_3$, alkoxy, aryl, aralkyl, heteroaralkyl, aryloxy, arylalkoxy, —OCF$_3$, —OCO-alkyl, COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

R$_1$ is —H;

X is —CO—, or —CS—;

R$_2$ and R$_3$, taken together with the attached nitrogen, form a 5- to 7-membered heterocyclic or heteroaromatic, ring containing from one to three heteroatoms selected from N, O or S, which may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$; and W is pyrrole, optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

wherein R$_a$ and R$_b$ are independently hydrogen, alkyl, cycloalkyl, haloalkyl, aryl, aralkyl, heteroaralkyl or heteroaryl.

2. A compound according to claim 1, wherein

A is phenyl;

R$_1$ is —H; and

R$_2$ and R$_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —C$_{1-6}$ alkyl, amino, aminoalkyl, hydroxyalkyl, alkoxyalkyl, heteroaryl, halogen, hydroxy, —CF$_3$, alkoxy, aryl, aralkyl, heteroaralkyl, aryloxy, arylalkoxy, —OCF$_3$, —OCO-alkyl, —OCO-alkylamino, —OCO-alkylamido, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, wherein R$_a$ and R$_b$ are independently hydrogen, alkyl, cycloalkyl, haloalkyl, aryl, aralkyl, heteroaralkyl or heteroaryl.

3. A compound of claim 1, which is 5-cyano-1H-pyrrole-2-carboxylic acid (2-piperidin-1-yl-phenyl)-amide, and pharmaceutically acceptable salts thereof.

4. A pharmaceutical composition, comprising a compound of claim 1 and a pharmaceutically acceptable carrier.

* * * * *